United States Patent [19]

Knifton

[11] Patent Number: 4,629,807

[45] Date of Patent: Dec. 16, 1986

[54] SELECTIVE SYNTHESIS OF ALIPHATIC DICARBOXYLIC ACID ESTERS USING PALLADIUM-PHOSPHINE OR PALLADIUM-ARSINE CATALYSTS

[75] Inventor: John F. Knifton, Austin, Tex.

[73] Assignee: Texaco Inc., White Plains, N.Y.

[21] Appl. No.: 826,642

[22] Filed: Feb. 6, 1986

[51] Int. Cl.⁴ .................... C07C 67/38; C07C 51/14
[52] U.S. Cl. ............................ 560/204; 502/171; 502/213; 560/190; 562/590; 562/595
[58] Field of Search ............. 562/590, 595; 560/204, 560/190; 502/171, 213

[56] References Cited

U.S. PATENT DOCUMENTS 4,230,881 10/1980 Romano et al. ............ 560/204 X
4,257,973 3/1981 Mrowca ..................... 560/204 X
4,414,409 11/1983 Waller ........................ 560/204 X Primary Examiner—Natalie Trousof
Assistant Examiner—Vera C. Clarke
Attorney, Agent, or Firm—Jack H. Park; Kenneth R. Priem; Cynthia L. Kendrick

[57] ABSTRACT

A process for preparing aliphatic dicarboxylic acid esters from aliphatic, non-conjugated dienes via carbonylation in the presence of a homogeneous palladium-phosphine catalyst or a palladium-phosphine melt catalyst.

19 Claims, No Drawings

SELECTIVE SYNTHESIS OF ALIPHATIC DICARBOXYLIC ACID ESTERS USING PALLADIUM-PHOSPHINE OR PALLADIUM-ARSINE CATALYSTS

This invention concerns a process for selective dicarbonylation of non-conjugated, alpha, omega-aliphatic dienes in the presence of a palladium catalyst selected from the group consisting of a homogenous palladium-phosphine catalyst system and a palladium phosphine "melt" catalyst. In particular dienes such as 1,7-octadiene and 1,5-hexadiene undergo dicarbonylation to yield product diacid esters comprising mainly three acid isomers; linear, monobranched and dibranched. The invention allows improved yields of the desired linear products.

BACKGROUND OF THE INVENTION

It is known in the art to use complexes of Pd(II) as homogeneous catalysts for the carbonylation of olefins. Generally these processes require a comparatively high pressure of carbon monoxide with a consequent need for expensive equipment.

A general review of the carbonylation of olefins using palladium complexes as catalysts appears in Angew, Chem. 80, 352, (1968) (International Edition, Vol. 7 (1968), p. 329) and references therein.

There is disclosed in U.S. Pat. No. 3,437,676 a process for the carbonylation of olefinically unsaturated compounds to form products selected from the group consisting of carboxylic acids and esters by reacting an olefinically unsaturated compound with carbon monoxide and with a hydroxy compound selected from the group consisting of water, alcohols and phenols in the presence of a catalyst, the improvement comprising employing a specific amount of a complex palladium salt having the formula $L_m PdX_n$ in which L denotes a member selected from the group consisting of organic phosphines, organic phosphites, ammonia, amines, nitriles and unsaturated hydrocarbons, X denotes an acid equivalent selected from the group consisting of chloride, bromide, sulfate, phosphate, acetate, nitrate, propionate and borate, m denotes an integer of from 1 to 4 and n denotes either the number 1 or 2.

U.S. Pat. No. 3,887,595 to Nozaki discloses a process of carbonylating olefinically unsaturated hydrocarbons of from 2 to 30 carbons, not including acetylenic or conjugated olefinic unsaturation, with carbon monoxide and at least one hydroxylic compound selected from the group consisting of water, alkanol and carboxylic acid in the presence of a catalyst consisting essentially of a zerovalent noble metal phosphine complex of the general formula $(R_3P)_n M$, wherein M is palladium or platinum, the improvement comprising producing predominately straight chain products.

In U.S. Pat. No. 3,919,272 there is disclosed a catalytic process for preparing linear saturated carboxylic products from alpha olefins having 3 to 40 carbon atoms by a process of heating alpha olefins with a $PdCl_2[As(C_6H_5)_3]_2$—$GeCl_2$ catalyst.

U.S. Pat. No. 3,952,034 discloses a process for carbonylation of olefins and acetylenes to a carboxylic acid or ester using a homogenous catalyst system comprising palladium together with iron or a metal of groups IVA, VA or IIIB, the catalyst being either a polynuclear complex incorporating both metals or a mixture of a soluble palladium salt and metal halide.

In EPA No. 0 055 875 an essentially halide-free palladium catalyst containing a triorganophosphine, in the absence of sodium acetate, is used for the carbonylation of an olefin.

European patent application No. 0 106 379 discloses a process for the carbonylation of olefinically unsaturated compounds with a palladium catalyst wherein the catalyst also contains at least 5 moles of phosphine and three aryl groups per gram atom of palladium.

None of the references in the prior art appears to address the specific problems of dicarbonylating non-conjugated, alpha, omega-aliphatic linear dienes, such as 1,7-octadiene, to produce linear aliphatic dicarboxylic acids and their derivatives. Further, in some of the catalyst systems there is a problem with metal plating and precipitation.

It would be an advance in the art to devise a catalyst system for producing aliphatic dicarboxylic acids in improved yield with an improved yield of desired linear aliphatic dicarboxylic acids. A palladium catalyst which could be recovered without usual amounts of metal plating and precipitation would also be an improvement: a palladium catalyst which exhibited improved solubilization under ambient conditions would be a further improvement over the art.

The product aliphatic diacids would be useful as corrosion inhibitors for antifreeze. The product diacids are comparable to sebacic acid, a commercial corrosion inhibitor. The product diacids should be less expensive than the sebacic acid.

SUMMARY OF THE INVENTION

This invention concerns a process for production of dicarboxylic acids with two carbons per molecule greater than the starting diene from non-conjugated, alpha, omega-aliphatic dienes and carbon monoxide in the presence of a palladium catalyst selected from the group consisting of a homogeneous palladium-phosphine catalyst and a palladium-phosphine melt catalyst.

A particular advantage of this system over the prior art is that improved yields of aliphatic dicarboxylic acids are obtained, including improved yields of the desired linear aliphatic dicarboxylic acids.

Other advantages include:
(1) Improved palladium catalyst recovery.
(2) Temperature staging with the homogeneous catalyst.
(3) Solubilization of the palladium catalyst components under ambient conditions.

DETAILED DESCRIPTION OF THE INVENTION

In the narrower and more preferred practice of this invention dicarboxylic acids are prepared by a process which comprises reacting non-conjugated dienes, an aliphatic monohydric alcohol and carbon monoxide in the presence of a palladium catalyst selected from the group consisting of a homogeneous palladium-phosphine or arsine catalyst, or a palladium-phosphine melt catalyst, wherein the improvements result from the added phosphine, at a temperature of at least 25° C. and a pressure of at least 50 psig until the desired products are formed.

Applicants have found that the addition of excess phosphine ligand to the palladium catalyst allows greater selectivity for linear acid ester products with selectivities greater than 60% (as in Example III). In practice, linear dicarboxylic acid esters containing two carbons per molecule more than the starting diene are produced by a process comprising:
  a. Mixing a non-conjugated diene with an alcohol and carbon monoxide in the presence of a palladium catalyst selected from the group consisting of a homogeneous phosphine or arsine ligand stabilized palladium catalyst, and a palladium-phosphine melt catalyst, wherein the improvements result from the added excess phosphine.
  b. Heating said reaction mixture at 25° C. or greater until substantial carbonylation of the non-conjugated diene to the desired linear aliphatic dicarboxylic acid ester and isolating the esters contained therein.

The reaction can best be described by the following equation, for 1,7-octadiene carbonylation to $C_{10}$ aliphatic dicarboxylic acid esters:

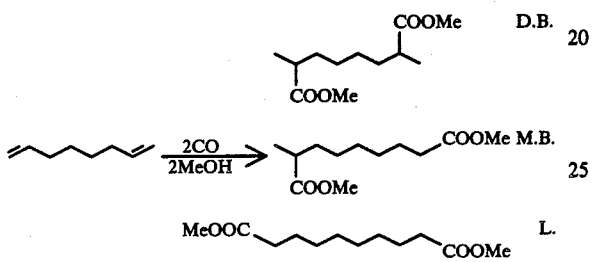

where L is the desired linear $C_{10}$-aliphatic dicarboxylic acid ester (in this case dimethyl sebacate), M.B. is the monobranched $C_{10}$-aliphatic dicarboxylic acid ester analog, and D.B. is the dibranched $C_{10}$-aliphatic dicarboxylic acid ester.

In order to present the inventive concept in the greatest possible detail, the following supplementary disclosure is submitted:

A. Process Sequence and Variations—In general, the components of the carbonylation reaction mixture including aliphatic monohydric alcohol, non-conjugated aliphatic diene, carbon monoxide, optional inert solvent and palladium-phosphine or arsine stabilized catalyst may be added in any sequence as long as good agitation is employed to provide a homogeneous mixture. For example, the following represent some variations insofar as the catalyst, sequence of CO pressurization and heating of the embodiment using the homogeneous palladium-ligand catalyst that may be made without departing from the inventive process. These modifications include:

1. The palladium-ligand catalyst may be preformed and added preformed to the reaction mixture.
  2. Preferably the catalyst is best formed in situ by the addition of the ligand stabilized palladium(II) salt plus excess ligand.
  3. After using either variation 1 or 2 the catalyst containing reaction mixture is pressurized with CO and heated. When an aliphatic monohydric alcohol is present, the ester of the carboxylic acid containing two more carbons will be formed. The formation of the ester is useful both in product applications and for rapid chromatographic analysis.
  4. After using either variation 1 or 2 the catalyst solution, non-conjugated diene and alcohol can be heated first under an inert atmosphere or a small pressure of CO (10–100 psig) then pressurized to the desired extent with carbon monoxide to form the desired dicarboxylic acid ester.
  5. A substantial process improvement that can be employed is where the palladium-ligand catalyst, diene, alcohol and optional inert solvent are heated to a moderate temperature (e.g. 100° C.) under a small pressure of CO, the pressure is raised to the desired extent with carbon monoxide, and the reaction mixture is held at temperature for a period of time, then the reaction temperature is raised to a higher level (e.g. 150° C.) for a period of time, with repressuring of the reactor with CO as needed. This process sequence is commonly referred to as temperature ramping.
  6. In the process embodiment using the palladium melt catalyst the palladium-phosphine catalysts are, prior to their catalytic use, first dispersed in a low melting quaternary phosphonium salt.

B. Quaternary Phosphonium Salt—The quaternary onium salt which may optionally be used in the catalyst composition may be any onium salt but is preferably one of those containing phosphorus, such as those of the formula:

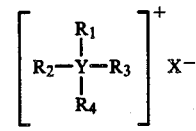

wherein Y is phosphorus, $R_1$, $R_2$, $R_3$ and $R_4$ are organic radicals, preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory.

Equally useful are the phosphonium salts containing phosphorus bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorus through the aryl function.

Illustrative examples of suitable quaternary onium salts include tetrabutylphosphonium bromide, heptyltriphenylphosphonium bromide, tetrabutylphosphonium iodide, tetrabutylphosphonium acetate, tetrabutylphosphonium nitrate, tetrabutylphosphonium chromate, tetraoctylphosphonium tetrafluoroborate, tetrahexylphosphonium acetate and methyl tri-n-butylphosphonium iodide.

C. Palladium-ligand catalyst combination—The use of palladium-ligand catalyst combinations is essential to the carbonylation process of this invention. The ligands used to stabilize the palladium may be selected from those donor ligands containing one or more tertiary phosphine or arsine donor atoms. Said ligands may be selected from the following groups:

1. Monodentate phosphine or arsine ligands, wherein each ligand molecule contains only one phosphorus or arsenic atom bonded to alkyl, aryl, aryloxy, alkaryl and substituted aryl radicals. Illustrative of such ligands are triphenylphosphine, tri-n-butylphosphine, triphenylarsine, dimethylphenylphosphine, tricyclohexylphosphine, tri-p-tolylphosphine, tri-o-tolyphosphine, tri(p-chlorophenyl)phosphine, and $P(OC_6H_5)_3$.

2. Also effective are phosphine and arsine ligands wherein each ligand molecule contains two or more phosphorus or arsenic atoms bonded to aryl, arlyoxy, alkaryl, and substituted aryl radicals. Illustrative of such ligands are 1,2-bis(diphenylphosphino)ethane, 1,3-bis(diphenylphosphino)propane, 1,4-bis(diphenylphosphino)butane, 1,5-bis(diphenylphosphino)pentane, 1,2-bis(diphenylarsino)ethane, tris(2-phenylphosphinoethyl)phosphine and bis(2-diphenylphosphinoethyl)phenylphosphine. These ligands are commonly referred to as bidentate or polydentate ligands.

3. A third possibility is the use of two or more different phosphine or arsine ligands selected from Classes 1 and 2, but particularly combinations thereof.

The molar ratio of palladium to phosphine or arsine ligand, employed as the catalyst precursor prior to diene carbonylation, may be varied over a wide range, from 1:1, to $1:10^3$ of Pd: P or As.

To ensure that the linear aliphatic dicarboxylic acid ester (L, eg. 1) is the predominant dicarboxylic acid derivative in this synthesis it is preferable:

a. To use a bidentate or polydentate phosphine or arsine ligand selected from the classes of ligands described supra, in the palladium-ligand catalyst precursor formulation, and/or b. To use an excess of monodentate phosphine or arsine ligand selected from the classes of ligands described supra. Here the palladium-phosphine or arsine molar ratio may vary from 1:2 to $1:10^3$.

The palladium source for the desired diene carbonylation is preferably a phosphine or arsine ligand-stabilized palladium halide complex. Particularly preferred as the palladium source for these synthesis is the bis(triphenylphosphine)palladium(n)chloride complex $PdCl_2(PPh_3)_2$, used in conjunction with other monodentate and bidentate phosphines, such as triphenylphosphine and 1,5-bis(diphenylphosphino)pentane. These catalyst combinations are illustrated by Examples I-III, and XVII, for the homogeneous palladium catalyst systems, and Examples XVIII to XXV for the palladium melt catalyst system.

D. Temperature required for carbonylation—The temperature range which can be employed for carbonylation is variable dependent upon other experimental factors including the non-conjugated diene employed, the pressure, the concentration and the particular choice of palladium catalyst among other things. Again using 1,7-octadiene as a typical diene and $PdCl_2(PPh_3)_2$—$PPh_3$ as a representative catalyst precursor, the range of operability is from 25° to 200° C. when superatmospheric pressures of 50 psig or more are employed. A narrower range of 90° C. to 160° C. represents the preferred temperature range when the aforementioned diene is dicarbonylated at about 3000 psig.

A preferred embodiment is where the reaction temperature is ramped, so that the first part of the diene carbonylation synthesis is conducted at a lower reaction temperature (e.g. 100° C.), and then the reaction temperature is raised to a higher level (e.g. 150° C.) for a period of time, with repressuring of the reaction with CO as needed. This process sequence is commonly referred to as temperature ramping.

The advantages of temperature ramping in the synthesis of aliphatic dicarboxylic acid esters from non-conjugated dienes using palladium-phosphine catalyst combinations are illustrated here by comparing Examples I and II with comparative Examples IIA and IIB. These advantages include:

a. Higher yields of desired aliphatic dicarboxylic acid ester product.

b. Improved recovery of the Pd catalyst complex in solution at the completion of the diene carbonylation sequence.

When the added phosphine ligand is used in molar excess, with respect to the starting palladium concentration, and the temperature ramping procedure is employed, the linear aliphatic dicarboxylic acid ester is the predominant product, there is no evidence of palladium metal plating, and there is quantitative Pd recovery in the product solution. These improvements are illustrated for the palladium-phosphine homogenous catalyst systems by Example III, and for the palladium-phosphine melt catalyst systems by Example XXII.

E. Pressure—Superatmospheric pressures of carbon monoxide of at least 50 psig are required for substantial conversion of the non-conjugated diene to the carboxylic acid (or ester) at temperatures of 25° to 200° C. using $PdCl_2(PPh_3)$—$PPh_3$ as the catalyst and 1,7-octadiene as the diene. At least a stoichiometric quantity of pressurized carbon monoxide is used, said stoichiometry being based upon the diene content in said mixture. The preferred pressure range is 500 to 5000 psig.

F. Reaction Times Required—As previously indicated in the analogous discussion on temperatures and pressures required in the reaction, experimental variables are important in arriving at reaction times. Generally substantial conversions (70% or higher) of the non-conjugated diene to the dicarboxylic acids can almost always be accomplished within total reaction times of twenty hours or less, with 2 to 8 hours total reaction times (for the temperature ramping mode) representing the more usual reaction time interval.

G. Non-conjugated dienes as Substrates—Non-conjugated, aliphatic dienes ranging in carbon content from three (3) up to 40 carbon atoms are employed. These diene substrates may be utilized neat or in conjunction with one or more inert background solvents such as p-dioxane. The dienes can be in the form of single, discrete compounds such as 1,4-cyclooctadiene, vinylcyclohexene, 2,5-norbornadiene and dicyclopentadiene, or in the form of mixture of dienes. In the latter case these comprise mixtures of $C_3$ to $C_{30}$ carbons containing non-conjugated dienes. Usually these mixtures have a spread of from 4 to 8 carbon atoms. Because of their relatively low cost, mixtures of non-conjugated, alpha, omega-aliphatic dienes ranging in carbon content from $C_5$ to $C_{13}$ and upwards are favored substrates for carbonylation wherein the ligand-stabilized palladium(II) homogeneous catalysts are employed at sufficiently elevated temperatures and pressures. Illustrative linear alpha, omega diene substrates which work well include 1,7-octadiene, 1,5-hexadiene, 1,9-decadiene, 1,19-elcosadiene and 1,13-tetradecadiene.

H. Alcohol Co-Reactant—If it is desired to prepare aliphatic dicarboxylic acid esters, an alcohol coreactant must be present in the reaction mixture with the diene substrate and carbon monoxide. The alcohol may be an aliphatic monohydric alkanol of up to 12 carbon atoms, a substituted alcohol, a phenol or a substitutued phenol. Suitable examples include methanol, ethanol, isopropanol, dodecanol, phenol, 2-chloroethanol, methylcyclohexanol and the like.

Alternatively, the alcohol may be polyol containing two or more hydroxyl groupings. Illustrative examples of suitable polyols include propylene glycol, neopentyl glycol, trimethylol propane and pentaerythritol. As indicated earlier the use of water produces the free acid.

I. Carbon Monoxide Environment—Insofar as can be determined the best selectivities and conversions of dienes to aliphatic dicarboxylic acids can be obtained within a reasonable reaction time by using a substantially carbon monoxide gaseous atmosphere. However, particularly in continuous operation, the carbon monoxide may be used in conjunction with from about 0 to 30% by volume of one or more inert gases such as nitrogen, argon, neon and the like without experiencing a substantial decrease in yield and selectivity.

J. Inert Solvents—The novel dicarbonylation is run most conveniently in the presence of an inert diluent. A variety of solvents can be used, including aromatics such as benzene, toluene and xylenes, halogenated aromatics including o-dichlorobenzene, ketones like acetone and methyl isobutyl ketone, ethers such as dimethoxyethane and p-dioxane and halogenated paraffins including ethylene dichloride and chloroform.

K. Selectivity—Selectivity as defined herein is the efficiency in catalyzing a desired dicarbonylation reaction relative to other undesired dicarbonylation reactions. In this instance dicarbonylation to the linear aliphatic dicarboxylic acid derivative is the desired conversion. Selectivity is usually expressed as a percentile and is calculated herein by determining the amount of linear dicarbonylated product formed, divided by the total amount of dicarbonylated products formed and multiplying the quotient obtained by 100.

L. Conversion—Conversion as defined herein is the efficiency in converting the non-conjugated dienes to useful products. Conversion is expressed as a percentile and is calculated herein by dividing the amount of diene consumed during dicarbonylation by the amount of diene originally charged and multiplying the quotient by 100.

M. Yield—Yield as defined herein is the efficiency in catalyzing a desired dicarbonylation reaction relative to other undesired reactions. In this instance, dicarbonylation to the dicarboxylic acid derivative is the desired conversion. Yield is usually expressed as a percentile and is calculated herein by determining the amount of linear, monobranched plus dibranched dicarboxylated product formed divided by the amount of diene charged and multiplying the quotient by 100.

N. By-products—As far as can be determined, without limiting the invention thereby, dicarbonylation of non-conjugated dienes catalyzed by the palladium(II) phosphine complexes leads to the formation of three isomers of the dicarboxylic acid ester formed: the linear, monobranched and dibranched. By-products include aliphatic monocarboxylic acids (M.E.) and isomerized olefins.

These by-products may be separated from the desired linear fatty acids or esters by the usual chemical or physical techniques.

O Identification Procedures—Where applicable identification is by one or more of the following analytical procedures: gas chromatography (g.c.), infrared, nuclear magnetic resonance and elemental analysis. Unless otherwise specified all percentages are by weight rather than volume and all temperatures are in centigrade rather than fahrenheit.

Having described the inventive process in general terms, Examples I through XVII are submitted to supply specific and illustrative embodiments of the method using the homogeneous palladium/phosphine catalyst. Examples XVIII through XXV illustrate the embodiment using the palladium "melt" catalyst.

Examples I-XVII and comparative Examples IIA and IIB illustrate the selective dicarbonylation of 1,7-octadiene and 1,5-hexadiene using various palladium-phosphine/arsine catalyst combinations. It may be noted that:

(1) In Example I, the $PdCl_2(PPh_3)_2$—$PPh_3$ combination, when employed in a temperature ramping mode, yields $C_{10}$ aliphatic dicarboxylic acid dimethyl ester in 94% yield and 38.4% concentration in the crude liquid product. The monobranched diacid ester (M.B.) is the predominant product isomer, 1,7-octadiene conversion is near quantitative, but palladium recovery in solution is only 4.8%.

(2) In Example II the $PdCl_2(PPh_3)_2$ complex in combination with the bidentate phosphine 1,5-bis(diphenylphosphino)pentane, and the temperature ramping procedure, yields the $C_{10}$ aliphatic dicarboxylic acid dimethyl ester in 93% yield and 38.6% conc. in the crude liquid product. But here the linear diacid ester (L) is the predominant product isomer and there is no evidence of palladium metal plating or precipitation. 1,7-octadiene conversion is quantitative.

(3) In comparative Examples IIA and IIB without the use of temperature ramping it is observed that there are:

(a) Lower yields of desired $C_{10}$ aliphatic dicarboxylic acid esters:
(b) Poorer recovery of Pd catalyst complex.

This is true for both the palladium-monodentate phosphine and the palladium monodentate phosphine/bidentate phosphine catalyst combination.

(4) In Example III, the use of excess bidentate phosphine leads to:

(a) Higher selectivity to desired linear $C_{10}$ aliphatic dicarboxylic acid ester.
(b) Solubilization of the Pd catalyst components under ambient conditions.
(c) Quantitative Pd recovery in the product solution.

(5) Other combinations of palladium/phosphines, both monodentate and bidentate, as well as bidentate arsines are also effective for this synthesis. Data are summarized in Table I. Both the desired $C_{10}$-aliphatic diacid esters (D.E.) and some $C_9$-aliphatic monoacid esters (M.E.) are being generated.

(6) Ineffective palladium catalyst combinations include:

(a) $PdCl_2$ alone—Example XV.
(b) $PdCl_2$ with trialkylphosphines like $PBu_3$—Example XIII.
(c) $PdCl_2$ and only bidentate phosphine, e.g. $Ph_2P(CH)_5PPh_2$—Example XIV.
(d) Halide-free $Pd(OAc)_2$ plus triphenylphosphine—Example XVI.

(7) Carbonylation of 1,5-hexadiene is illustrated in Example IV.

(8) Scale up of the dicarbonylation of 1,7-octadiene and isolation of the product $C_{10}$ aliphatic dicarboxylic acid dimethyl esters is illustrated in Example XVII. Again the linear $C_{10}$ acid ester is the predominant product fraction, and there is no evidence of palladium metal plating or precipitation.

EXAMPLE I

This example illustrates the selective dicarbonylation of 1,7-octadiene catalyzed by a palladium-monodentate phosphine catalyst, using a temperature ramping operative procedure.

To a 450-ml capacity reactor fitted with heating, agitation, and gas pressure facilities is charged a mixture of:
10.0 g of 1,7-octadiene (90.7 mmoles)
30.0 g of p-dioxane
0.70 g of bis(triphenylphosphine)palladium(II) chloride (1.0 mmole)
0.13 g of triphenylphosphine (0.5 mmole)
6.4 g of methanol (200 mmole)

The reactor was sealed, flushed with carbon monoxide, pressured to 300 psi with CO and heated to 100° C. with agitation. The pressure in the reactor was then raised to 3000 psi with CO from an outside source and the mixture was held at 100° C. for 4 hours. Additional CO is added as required in order to maintain the reactor pressure at 3000 psi. After 4 hours at 100° C., the temperature in the reactor was raised to 150° C. and held at that temperature, with agitation, for an additional 4 hours. Again, additional CO was added to the reactor as needed in order to maintain the pressure at 3000 psi.

Upon cooling, the excess gas is vented from the reactor, and 52.2 g of yellow colored liquid product was recovered. Analysis of the liquid product by GLC showed it to comprise:
13.3% dibranched $C_{10}$ acid dimethyl ester—Structure D.B.
19.1% monobranched $C_{10}$ acid dimethyl ester—Structure M.B.
6.0% linear $C_{10}$ acid dimethyl ester—Structure L
58.7% p-dioxane
0.1% unreacted methanol
0.1% water

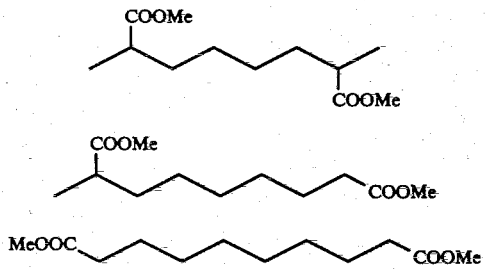

The total concentration of $C_{10}$-aliphatic acid dimethyl ester = 38.4%
The estimated yield of total $C_{10}$-aliphatic acid dimethyl ester =

$$\frac{38.4 \times (52.2 - 0.8) \times 10^3}{100 \times 230.3 \times 90.7} \times 100 = 94\%$$

where 230.3 is the formula weight of the $C_{10}$ aliphatic acid dimethyl ester.

The $C_{10}$ aliphatic acid dimethyl ester fraction was isolated by distillation under vacuo of the crude liquid product and identified by nmr, FTIR, etc.

The crude liquid product was also analyzed for palladium content and found to contain 98 ppm.

The estimated recovery of palladium in solution was 4.8%.

The remainder of the palladium was recovered as a black, insoluble, solid.

EXAMPLE II

This example illustrates the selective dicarbonylation of 1,7-octadiene catalyzed by a palladium-monodentate phosphine/bidentate phosphine catalyst combination.

Following the procedures of Example I, a 450-ml capacity reactor was charged with a mixture of:
10.0 g of 1,7-octadiene (90.7 mmoles)
30.0 g of p-dioxane
0.70 g of bis(triphenylphosphine)palladium(II) chloride (1.0 mmole)
0.44 g of 1,5-bis(diphenylphosphino)pentane (1.0 mmole)
6.4 g of methanol (200 mmole)

The reactor was sealed, flushed with carbon monoxide, pressured to 300 psi with CO and heated to 100° C. with agitation. The pressure in the reactor was then raised to 3000 psi with CO from an outside source and the mixture was held at 100° C. for 4 hours. Additional CO was added as required in order to maintain the reactor pressure at 3000 psi. After 4 hours at 100° C., the temperature in the reactor was raised to 150° C. and held at that temperature, with agitation, for an additional 4 hours. Again, additional CO was added to the reactor as needed in order to maintain the pressure at 3000 psi.

Upon cooling, the excess gas was vented from the reactor, and 51.4 g of yellow colored liquid product was recovered. Analysis of the liquid product by GLC showed it to comprise:
0.6% aliphatic $C_9$ acid monomethyl ester (M.E.)
3.8% dibranched $C_{10}$ acid dimethyl ester (D.B.)
16.8% monobranched $C_{10}$ acid dimethyl ester (M.B.)
18.0% linear $C_{10}$ acid dimethyl ester (L)
58.3% p-dioxane
0.1% unreacted methanol
0.1% water The total concentration of $C_{10}$ aliphatic acid dimethyl ester = 38.6%. The estimated yield of total $C_{10}$ aliphatic acid dimethyl ester = 93%. Selectivity to linear $C_{10}$ acid dimethyl ester (L) = 47%.

It is noted that among the three $C_{10}$ aliphatic acid dimethyl esters produced, the linear isomer (L) predominates in this example using the palladium-monodentate phosphine/bidentate phosphine catalyst combination.

Note, also in this example, there is no palladium-containing black precipitate in the crude product mixture. The palladium is recovered as a yellow palladium-phosphine complex.

COMPARATIVE EXAMPLE IIA

This comparative example illustrates the dicarbonylation of 1,7-octadiene catalyzed by the same palladium-monodentate phosphine catalyst of Example I but without using the temperature ramping procedure.

To the reactor of Example I is charged the same mixture of:
10.0 g of 1,7-octadiene (90.7 mmoles)
30.0 g of p-dioxane 0.70 g of bis(triphenylphosphine)palladium(II)chloride (1.0 mmole)
0.13 g of triphenylphosphine (0.5 mmole)
6.4 g of methanol (200 mmole)

The reactor was sealed, flushed with carbon monoxide, pressured to 300 psi with CO and heated to 150° C. with agitation. The pressure in the reactor was then raised to 3000 psi with CO from an outside source and the mixture was held at 150° C. for 4 hours. Additional CO is added as required in order to maintain the reactor pressure at 3000 psi.

Upon cooling, the excess gas was vented from the reactor, and 50.0 g of yellow colored liquid product was recovered. Analysis of the liquid product by GLC showed it to comprise:
10.3% aliphatic $C_9$ acid monomethyl ester (M.E.)
13.9% dibranched $C_{10}$ acid dimethyl ester (D.B.)
9.4% monobranched $C_{10}$ acid dimethyl ester (M.B.)
2.0% linear $C_{10}$ acid dimethyl ester (L)
60.3% p-dioxane
4.6% unreacted methanol
0.3% water The total concentration of $C_{10}$ aliphatic acid dimethyl ester=23.3%. The estimated yield of total $C_{10}$ aliphatic acid dimethyl ester=55%.

It is noted, in this comparative example, without using the temperature ramping procedure of Example I, the yield of desired $C_{10}$ aliphatic acid dimethyl ester is substantially reduced in comparison with the yields of the same product reported in Example I.

COMPARATIVE EXAMPLE IIB

This comparative example illustrates the dicarbonylation of 1,7-octadiene catalyzed by the same palladium-monodentate phosphine/bidentate phosphine catalyst combination of Example II but without the temperature ramping procedure.

To the reactor of Example II is charged the same mixture of:
10.0 g of 1,7-octadiene (90.7 mmoles)
30.0 g of p-dioxane
0.70 g of bis(triphenylphosphine)palladium(II) chloride (1.0 mmole)
0.44 g of 1,5-bis(diphenylphosphino)pentane (1.0 mmole)
6.4 g of methanol (200 mmole)

The reactor was sealed, flushed with carbon monoxide, pressured to 300 psi with CO and heated to 150° C. with agitation. The pressure in the reactor was then raised to 3000 psi with CO from an outside source and the mixture was held at 150° C. for 4 hours. Additional CO is added as required in order to maintain the reaction pressure at 3000 psi.

Upon cooling, the excess gas is vented from the reactor and 52.2 c of yellow colored liquid product was recovered. Analysis of the liquid product by GLC showed it to comprise:
2.8% aliphatic $C_9$ acid monomethyl ester—Structure M.E.
10.4% dibranched $C_{10}$ acid dimethyl ester—Structure D.B.
16.3% monobranched $C_{10}$ acid dimethyl ester—Structure M.B.
7.1% linear $C_{10}$ acid dimethyl ester (L)
61.0% p-dioxane
1.6% unreacted methanol
0.2% water The total concentration of $C_{10}$ aliphatic acid dimethyl ester=33.8%.
The estimated yield of total $C_{10}$ aliphatic acid dimethyl ester=83%.

The crude liquid product was also analyzed for palladium content: 1060 ppm.

The estimated recovery of palladium in solution=52%.

The remainder of the palladium was recovered as a black, insoluble solid.

Note in this comparative example, without the temperature ramping procedure of Example II:
(a) The yield of desired $C_{10}$ aliphatic acid dimethyl ester was lower.
(b) The palladium catalyst complex recovery was substantially poorer.

EXAMPLE III

This example illustrates the improved selective dicarbonylation of 1,7-octadiene catalyzed by a palladium-monodentate phosphine/bidentate phosphine catalyst combination using an excess of the bidentate phosphine component.

Following the procedure of Example II, the reactor was charged with a mixture of:
10.0 g of 1,7-octadiene (90.7 mmoles)
30.0 g of p-dioxane
0.70 g of bis(triphenylphosphine)palladium(II) chloride (1.0 mmole)
2.20 g of 1,5-bis(diphenylphosphino)pentane (5.0 mmole)
6.4 g of methanol (200 mmole)

Upon stirring this mixture under a CO atmosphere at ambient temperatures all the solid catalyst components dissolved within a few minutes to form a clear yellow solution.

The reactor was then sealed, flushed with carbon monoxide, pressured to 300 psi with CO and the conversion to $C_{10}$ acid esters conducted as in Example II. 51.2 g of a yellow-colored, clear liquid were removed. Analysis of this liquid product by GLC showed it to comprise:
2.1% aliphatic $C_9$ acid monomethyl ester (M.E.)
1.5% dibranched $C_{10}$ acid dimethyl ester (D.B.)
12.2% monobranched $C_{10}$ acid dimethyl ester (M.B.)
23.5% linear $C_{10}$ acid dimethyl ester (L)
58.5% p-dioxane
0.2% methanol
0.3% water The total concentration of $C_{10}$ aliphatic acid dimethyl ester=37.2%.
The estimated yield of total $C_{10}$ aliphatic acid dimethyl ester=86%.
The estimated selectivity to linear $C_{10}$ aliphatic acid dimethyl ester=63%.

The crude liquid product was also analyzed for palladium content and found to contain 2350 ppm.

Estimated recovery of palladium in solution=>99%.

It should be noted that of the three $C_{10}$ aliphatic acid dimethyl esters produced, the linear isomer (L) predominates and in this example the ratio is calculated as follows:

$$\frac{L}{D.B. + M.B.} = \frac{23.5}{1.5 = 12.2} = 1.7$$

EXAMPLE IV

This example illustrates the selective dicarbonylation of 1,5-hexadiene catalyzed by the palladium-monodentate phosphine/bidentate phosphine catalyst combination.

To the reactor of Example II was charged the mixture of:
10.0 g of 1,5-hexadiene (121.7 mmoles)
30.0 g of p-dioxane
0.70 g of bis(triphenylphosphine)palladium(II) chloride (1.0 mmole)
0.44 g of 1,5-bis(diphenylphosphino)pentane (1.0 mmole)
6.4 g of methanol (200 mmole)

The reactor was sealed, flushed with carbon monoxide, pressured to 300 psi with CO and the conversion of the 1,5-hexadiene to acid esters conducted as in Example II.

52.9 g of red-colored liquid were recovered. Analysis of this liquid product by GLC showed it to comprise:
34.8% $C_8$ acid dimethyl esters
61.4% p-dioxane
0.7% unreacted methanol
0.1% water temperature in the reactor was raised to 150° C. and held at that temperature, with agitation, for an additional 14 hours. Again, additional CO was added to the reactor as needed in order to maintain the pressure at 3000 psi.

Upon cooling, the excess gas was vented from the reactor, and 1802.0 g of red liquid product was recovered. There were no solid products. Analysis of the liquid product by GLC showed it to comprise:
1.6% dibranched $C_{10}$ acid dimethyl ester (D.B.)
9.6% monobranched $C_{10}$ acid dimethyl ester (M.B.)
13.2% linear $C_{10}$ acid dimethyl ester (L)
66.6% p-dioxane
8.0% unreacted methanol
Estimated selectivity to $C_{10}$ acid dimethyl ester(L) = 54%

The crude liquid product was stripped of solvent on a rotary evaporator and the residual liquid subject to fractional distillation in vacuo.

The fraction (315.8 g) boiling at 115°–120° C. (0.7–0.8 mm Hg) comprised:
9.6% dibranched $C_{10}$ acid dimethyl ester (D.B.)
47.4% monobranched $C_{10}$ acid dimethyl ester (M.B.)
40.4% linear $C_{10}$ acid dimethyl ester (L)

A second distillate fraction (7.58 g) boiling at

TABLE I

SELECTIVE 1,7-OCTADIENE CARBONYLATION[a]

| Example | Catalyst Combination | M.E. | D.B. | M.B. | L. | Total | MeOH | p-Dioxane | H₂O | Yield (mole %) | Pd-Complex Recovery % |
|---|---|---|---|---|---|---|---|---|---|---|---|
| I | PdCl₂(PPh₃)₂—PPh₃ | | 13.3 | 19.1 | 6.0 | 38.4 | 0.1 | 58.7 | 0.1 | 94 | 4.8 |
| II | PdCl₂(PPh₃)₂—Ph₂P—(CH₂)₅PPh₂ | 0.6 | 3.8 | 16.8 | 18.0 | 38.6 | 0.1 | 58.3 | 0.1 | 93 | >95 |
| V | PdCl₂[P(p-CH₃Ph)₃—P(p-CH₃Ph)₃ | 0.7 | 12.8 | 17.7 | 6.6 | 37.1 | | 59.0 | 0.1 | 84 | 69 |
| VI | PdCl₂(PMe₂Ph)₂—PMe₂Ph | | 0.2 | 1.0 | 0.5 | 2.7 | 8.8 | 76.4 | 0.2 | 5.7 | 86 |
| VII | PdCl₂(PBu₃)₂—PBu₃ | | 1.6 | 4.2 | 2.4 | 8.2 | 7.0 | 68.3 | 0.1 | 19 | >99 |
| VIII | PdCl₂(PPh₃)₂—Ph₂P—(CH₂)PPh₂ | 15.3 | 2.8 | 6.1 | 3.3 | 12.2 | 4.2 | 67.0 | 0.2 | 27 | >95 |
| IX | PdCl₂(PPh₃)₂—Ph₂P—(CH₂)₃PPh₂ | | 10.3 | 18.0 | 8.3 | 36.6 | 0.1 | 59.5 | 0.2 | 89 | >95 |
| X | PdCl₂(PPh₃)₂—Ph₂P—(CH₂)₄PPh₂ | 8.2 | 3.4 | 12.5 | 12.6 | 28.5 | 2.0 | 60.7 | 0.1 | 68 | >95 |
| XI | PdCl₂(PPh₃)₂—Ph₂As—(CH₂)₂AsPh₂ | 12.6 | 6.2 | 10.7 | 5.0 | 21.4 | 2.4 | 61.4 | 0.3 | 52 | 49 |
| XII | PdCl₂—PPh₃ | | 8.7 | 19.5 | 11.1 | 39.4 | 0.1 | 57.8 | 0.2 | 93 | 71 |
| XIII | PdCl₂—PBu₃ | | | | | <0.1 | 13.6 | 84.5 | 0.1 | <1 | >99 |
| XIV | PdCl₂—Ph₂P(CH₂)₃PPh₂ | 5.2 | | | | 0.1 | 12.8 | 80.5 | 0.3 | <1 | 50 |
| XV | PdCl₂ | | | | | <0.1 | 13.7 | 85.9 | 0.3 | <1 | <2 |
| XVI | Pd(oAc)₂—PPh₃ | | | | | <0.1 | 14.5 | 83.9 | 0.3 | <1 | 52 |

[a]Synthesis conditions as per Example I

EXAMPLE XVII

A one gallon capacity reactor fitted with heating, agitation and gas pressuring facilities was charged with a mixture of:
220.4 g of 1,7-octadiene (2.0 moles)
1200.0 g of p-dioxane
28.0 g of bis(triphenylphosphine)palladium(II) chloride (40 mmole)
17.6 g of 1,5-bis(diphenylphosphino)pentane (40 mmole)
256.0 g of methanol (8.0 mole)

The reactor was sealed, flushed with carbon monoxide, pressured to 300 psi with CO and heated to 100° C. with agitation. The pressure in the reactor was then raised to 3000 psi with CO from an outside source and the mixture was held at 100° C. for 4 hours. Additional CO was added as required in order to maintain the reactor pressure at 3000 psi. After 4 hours at 100° C., the 120°–128° C. (1.0–1.2 mm Hg) comprised:
20.8% monobranched $C_{10}$ acid dimethyl ester (M.B.)
78.8% linear $C_{10}$ acid dimethyl ester (L)

The estimated yield of total isolated $C_{10}$ aliphatic acid dimethyl ester = 83 mole %.

Of the three $C_{10}$ aliphatic acid dimethyl esters produced, the linear isomer (L) predominated, and in this case the ratio of the crude liquid was:

$$\frac{13.2}{9.6} = \frac{1.6}{1.2}$$

Examples XVIII–XXV illustrate the selective dicarbonylation of 1,7-octadiene and 1,5-hexadiene using various palladium-phosphine catalyst combinations dispersed in quaternary phosphonium salts. It may be noted that:

(1) In Example XVIII, using the PdCl$_2$(PPh$_3$)$_2$—PPh$_3$/Bu$_4$PBr 'melt' catalyst precursor, the linear and branched C$_{10}$-aliphatic carboxylic acid dimethyl ester products are generated in 48.9% concentration and 52% mole yield with >99% palladium recovery in solution. There is no palladium precipitate or plating during this synthesis.

(2) In Example XXI, 1,5-hexadiene is carbonylated to the corresponding C$_8$-aliphatic dicarboxylic acid esters.

(3) Other palladium-phosphine/quaternary phosphonium halide catalyst compositions are illustrated in Examples XIX, XXII, and XXIII.

(4) The linear C$_{10}$-aliphatic dicarboxylic acid dimethyl ester (L) makes up the largest part (43%) of the total C$_{10}$-aliphatic dicarboxylic acid dimethyl ester product fraction in Example XXII where the catalyst precursor comprises PdCl$_2$(PPh$_3$)$_2$ plus excess triphenylphosphine.

(5) Scale up of these syntheses with product ester isolation is illustrated in Examples XXIV and XXV.

EXAMPLE XVIII

This example illustrates a typical preparative procedure.

A 450-ml capacity reactor fitted with heating, pressuring and agitation means was charged with a mixture of:

10.0 g of 1,7-octadiene (90.7 mmoles)
0.70 g of bis(triphenylphosphine)palladium(II) chloride (1.0 mmole)
0.13 g of triphenylphosphine (0.5 mmole)
6.4 g of methanol (200 mmole)
30.0 g of tetrabutylphosphonium bromide The reactor was flushed with carbon monoxide, pressured to 300 psi with CO and heated to 100° C. with agitation. The total pressure was then raised to 3000 psi using CO from a large reservoir and the reactor held at temperature for four hours. Additional CO was added as required in order to maintain the reactor pressure at 3000 psi. The temperature of the reaction mix was then raised to 150° C. and held at 150° C. for 4 hours. Again, additional CO was added as required in order to maintain the reactor pressure at 3000 psi.

Upon cooling, the excess gas was bled off, and 53.1 g of red-colored liquid product were recovered. Analysis of this product showed the organic fraction to comprise:

11.9% dibranched C$_{10}$-aliphatic dicarboxylic acid dimethyl ester (D.B.)
24.1% monobranched C$_{10}$-aliphatic dicarboxylic acid dimethyl ester (M.B.)
12.9% linear C$_{10}$-aliphatic dicarboxylic acid dimethyl ester (L)
15.1% C$_9$-aliphatic monocarboxylic acid methyl ester (M.E.)
<1% unreacted methanol
0.1% water The estimated yield of total C$_{10}$ aliphatic dicarboxylic acid dimethyl ester (FW, 230.3) =

$$\frac{48.9(53.1 - 30.8) \times 10^3 \times 100}{100 \times 230.3 \times 90.7} = 52\%$$

Palladium recovery in solution was 2140 ppm.
Estimated palladium recovery was >99%.

There was no palladium precipitation or plating during these syntheses.

EXAMPLE XIX

Using the procedures and equipment of Example XVIII, the 450 ml reactor was charged with a mixture of:

10.0 g of 1,7-octadiene (90.7 mmole)
0.70 g of bis(triphenylphosphine)palladium(II) chloride (1.0 mmole)
0.13 g of triphenylphosphine (0.5 mmole)
6.4 g of methanol (200 mmole)
30.0 g of tetrabutylphosphonium chloride Upon completion of the carbonylation, the liquid product (53.4 g) was analyzed. The organic fraction comprised:
44.0% C$_{10}$ aliphatic dicarboxylic acid dimethyl ester
17.2% C$_9$ aliphatic monocarboxylic acid methyl ester
<1% unreacted methanol
0.1% water The estimated yield of total C$_{10}$ aliphatic dicarboxylic acid dimethyl ester was 48 mole %.

EXAMPLE XX

Using the reactor of Example I, and a charge of:
10.0 g of 1,7-octadiene
0.70 g of bis(triphenylphosphine)palladium(II) chloride (1.0 mmole)
0.13 g of triphenylphosphine (0.5 mmole)
6.4 g of methanol (200 mmole)
30.9 g of tetrabutylphosphonium bromide The reactor was flushed with CO, pressured to 300 psi and heated to 120° C. with agitation. The total pressure was then raised to 3000 psi using a CO supply from a large reservoir, and the reactor held at temperature for 4 hours. Additional CO was added as required in order to maintain the reactor pressure at 3000 psi.

Upon cooling, the excess pressure was released, and 53.6 g of liquid product were recovered. Analysis of this material showed the organic fraction to comprise:
20.4% dibranched C$_{10}$-aliphatic dicarboxylic acid dimethyl ester
37.1% monobranched C$_{10}$-aliphatic dicarboxylic acid dimethyl ester
20.3% linear C$_{10}$-aliphatic dicarboxylic acid dimethyl ester
2.8% C$_9$-aliphatic monocarboxylic acid methyl ester.
0.3% unreacted methanol
0.3% water The estimated yield of total C$_{10}$-aliphatic dicarboxylic acid dimethyl ester was 85 mole %. Palladium recovery in solution was: 2490 ppm.

Estimated palladium recovery was >99%.

EXAMPLE XXI

Using the procedures and equipment of Example I, the reactor was charged with a mixture of:
10.0 g of 1,5-hexadiene (122 mmole) 0.70 g of bis(triphenylphosphine)palladium(II) chloride (1.0 mmole)
0.13 g of triphenylphosphine (0.5 mmole)
6.4 g of methanol (200 mmole)
30.0 g of tetrabutylphosphonium bromide Upon completion of the carbonylation, the liquid product (54.9 g) was analyzed. The organic fraction comprised:
40.7 % C$_8$ aliphatic dicarboxylic and dimethyl ester
2.9 % C$_7$ aliphatic monocarboxylic and methyl ester
<1% unreacted methanol 0.1% water

EXAMPLE XXII

Using the procedures and equipment of Example I, the reactor was charged with a mixture of:
10.0 g of 1,7-octadiene (90.7 mmole)
0.70 g of bis(triphenylphosphine)palladium chloride (1.0 mmole)
2.62 g of triphenylphosphine (10.0 mmole)
6.4 g of methanol (200 mmole)
30.0 g of tetrabutylphosphonium bromide Upon completion of the carbonylation, the liquid product (51.3 g) was analyzed. The organic fraction included:
8.3% $C_{10}$-aliphatic dicarboxylic acid dimethyl ester
25.0% $C_9$-aliphatic monocarboxylic acid methyl ester In this example the linear $C_{10}$-aliphatic dicarboxylic acid dimethyl ester (L) comprised the largest part (43%) of the total $C_{10}$-aliphatic dicarboxylic acid dimethyl ester product fraction.

EXAMPLE XXIII

Using the reactor and procedures of Example XVIII, the charge in this case was:
10.0 g of 1,7-octadiene (90.7 mmole)
0.70 g of bis(triphenylphosphine)palladium(II) chloride (1.0 mmole)
2.20 g of bis 1,5-(diphenylphosphino)pentane (5.0 mmole)
6.4 g of methanol (200 mmole)
30.4 g of tetrabutylphosphonium bromide Upon completion of the carbonylation, the liquid product (48.9 g) was analyzed. The organic fraction contained a small, but detectable, amount of $C_{10}$-aliphatic dicarboxylic acid dimethyl ester.

EXAMPLE XXIV

A one gallon stirred clave was charged with a mixture of:
220.4 g of 1,7-octadiene (2.0 mmole)
28.0 g of bis(triphenylphosphine)palladium(II)chloride (40 mmole)
5.2 g of triphenylphosphine (20 mmole)
256.0 g of methanol (200 mmole)
1200.0 g of tetrabutylphosphonium bromide The reactor was flushed with carbon monoxide, pressured to 300 psi with CO and heated to 100° C. with agitation. The total pressure was then raised to 3000 psi with CO and the reactor held at temperature for four hours. Additional CO was added as required in order to maintain the reactor pressure at 3000 psi. The temperature of the reaction mix was then raised to 150° C. and held at 150° C. for 14 hours. Again, additional CO was added as required in order to maintain the reactor pressure at 3000 psi.

Upon cooling, the excess gas was bled off, and 1922 g of liquid product were recovered. Analysis of this product showed the organic fraction to comprise:
19.3% $C_{10}$-aliphatic dicarboxylic acid dimethyl ester
0.4% $C_9$-aliphatic monocarboxylic acid monomethyl ester The crude liquid product was fractionally distilled under vacuum. The distillate fraction (44 g) boiling at ca. 110° C. (1.5-2.0 mm Hg) comprised:
63.2% dibranched $C_{10}$-aliphatic dicarboxylic acid dimethyl ester
19.8% monobranched $C_{10}$-aliphatic dicarboxylic acid dimethyl ester The distillate fraction (53 g) boiling at 118°-122° C. (1.6-2.2 mm Hg) comprised:
36.0% dibranched $C_{10}$-aliphatic dicarboxylic acid dimethyl ester
47.3% monobranched $C_{10}$-aliphatic dicarboxylic acid dimethyl ester
6.7% linear $C_{10}$-aliphatic dicarboxylic acid dimethyl ester

EXAMPLE XXV

A one gallon stirred clave was charged with a mixture of:
220.4 g of 1,7-octadiene (2.0 mmole)
28.0 g of bis(triphenylphosphine)palladium(II)chloride (40 mmole)
5.2 g of triphenylphosphine (20 mmole)
192.0 g of methanol (6.0 mmole)
660.0 g of tetrabutylphosphonium bromide The reactor was flushed with carbon monoxide, pressured at 300 psi with CO and heated to 100° C. with agitation. The total pressure was then raised to 3000 psi with CO and the reactor held at temperature for 14 hours. Additional CO was added as required in order to maintain the reactor pressure at 3000 psi. The temperature of the reaction mix was then raised to 150° C. and held at 150° C. for 14 hours. Again, additional CO was added as required in order to maintain the reactor pressure at 3000 psi.

Upon cooling, the excess gas was bled off and 1213.8 g of liquid product was recovered. Analysis of this product showed the organic fraction to comprise:
61.9% $C_{10}$-aliphatic dicarboxylic acid dimethyl ester The crude liquid product was fractionally distilled under vacuum. The distillate fraction (227 g) boiling at 115°-119° C. (0.6-1.2 mm Hg) comprised:
35.0% dibranched $C_{10}$-aliphatic dicarboxylic acid dimethyl ester
48.0% monobranched $C_{10}$-aliphatic dicarboxylic acid dimethyl ester
16.9% linear $C_{10}$-aliphatic dicarboxylic acid dimethyl ester A second distillate fraction (51 g) boiling at 118°-120° C. (1.2 mm Hg) comprised:
16.9% dibranched $C_{10}$-aliphatic dicarboxylic acid dimethyl ester
62.3 monobranched $C_{10}$-aliphatic dicarboxylic acid dimethyl ester
21.2% linear $C_{10}$-aliphatic dicarboxylic acid dimethyl ester Estimated yield of isolated $C_{10}$-aliphatic dicarboxylic acid dimethyl ester was 60 mole %.

What is claimed is:

1. A process for producing aliphatic dicarboxylic acids and esters by reacting nonconjugated, alpha, omega-aliphatic dienes ranging in carbon content from $C_5$ to $C_{13}$ and carbon monoxide in the presence of a palladium-phosphine or a palladium-arsine catalyst at a pressure of at least 50 psig and a temperature of 25° C. to 200° C.

2. The process of claim 1 wherein the alpha, omega-aliphatic dienes are selected from the group consisting of 1,7-octadiene, 1,5-hexadiene and 1,9-decadiene.

3. The process of claim 1 wherein the products of said reaction are dicarboxylic acid esters and the process is conducted in the presence of a monohydric alcohol coreactant.

4. The process of claim 3 wherein the monohydric alcohol is selected from the group consisting of methanol, ethanol, isopropanol and dodecanol.

5. The process of claim 1 wherein the palladium-phosphine catalyst is comprised of a phosphine ligand-stabilized palladium(II) complex plus an excess of phosphine ligand.

6. The process of claim 5 wherein the phosphine ligand-stabilized palladium(II) complex is selected from the group including bis(triphenylphosphine)palladium(II) chloride, bis(tri-n-butylphosphine)palladium(II) chloride, bis[tri(p-chlorophenyl)phosphine]palladium(II) chloride and bis(dimethylphenylphosphine)palladium(II) chloride.

7. The process of claim 5 wherein the excess phosphine is a monodentate phosphine selected from the group including triphenylphosphine, tri-n-butylphosphine, tri(p-chlorophenyl)phosphine.

8. The process of claim 5 wherein the excess phosphine is a bidentate phosphine selected from the group including 1,2-bis(diphenylphosphino)ethane, 1,3-bis(diphenylphosphino)propane, 1,4-bis(diphenylphosphino)butane and 1,5-bis(diphenylphosphino)pentane.

9. The process of claim 1 wherein the arsine is selected from the group including triphenylarsine and 1,2-bis(diphenylarsino)ethane.

10. The process of claim 1 wherein the palladium-phosphine catalyst is dispersed in a quaternary phosphonium salt.

11. The process of claim 10 wherein the quaternary phosphonium salt is selected from the group including tetrabutylphosphonium bromide and tetrabutylphosphonium chloride.

12. The process of claim 1 wherein the palladium-phosphine catalyst is solubilized in an inert solvent.

13. The process of claim 12 wherein the inert solvent is p-dioxane.

14. The process of claim 1 wherein predominant aliphatic dicarboxylic acid ester is a linear aliphatic dicarboxylic acid ester.

15. The process of claim 14 wherein the palladium-phosphine catalyst is bis(triphenylphosphine)palladium(II) chloride plus triphenylphosphine.

16. The process of claim 14 wherein the palladium phosphine catalyst is bis(triphenylphosphine)palladium(II) chloride plus 1,5-bis(diphenylphosphino)pentane.

17. The process of claim 1 wherein the operating pressure is between 500 and 5000 psig.

18. The process of claim 1 wherein the operating temperature is between 90° and 160° C.

19. The process of claim 18 wherein the desired synthesis is conducted at two different temperatures, using a temperature ramping procedure wherein the two operating temperatures are about 100° C. and about 150° C.

* * * * *